(12) United States Patent
Gérard et al.

(10) Patent No.: US 11,810,224 B2
(45) Date of Patent: Nov. 7, 2023

(54) METHOD AND SYSTEM FOR TRANSPOSING MARKERS ADDED TO A FIRST ULTRASOUND IMAGING MODE DATASET TO A SECOND ULTRASOUND IMAGING MODE DATASET

(71) Applicant: GE Precision Healthcare LLC, Wauwatosa, WI (US)

(72) Inventors: Olivier Philippe Gérard, Oslo (NO); Alf Grini, Oslo (NO); Andreas Ziegler, Oslo (NO); Benjamin Fermann, Oslo (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 217 days.

(21) Appl. No.: 17/179,195

(22) Filed: Feb. 18, 2021

(65) Prior Publication Data

US 2022/0262044 A1 Aug. 18, 2022

(51) Int. Cl.
| G06T 7/70 | (2017.01) |
| G06T 7/00 | (2017.01) |
| G06T 11/00 | (2006.01) |
| A61B 8/00 | (2006.01) |

(52) U.S. Cl.
CPC .............. *G06T 11/00* (2013.01); *A61B 8/463* (2013.01); *A61B 8/466* (2013.01); *A61B 8/468* (2013.01); *G06T 7/0012* (2013.01); *G06T 7/70* (2017.01); *G06T 2200/24* (2013.01); *G06T 2207/10132* (2013.01); *G06T 2207/30004* (2013.01); *G06T 2207/30204* (2013.01)

(58) Field of Classification Search
CPC ......... G06T 11/00; G06T 7/70; G06T 7/0012; G06T 2200/24; G06T 2207/10132; G06T 2207/30004; G06T 2207/30204; A61B 8/463; A61B 8/466; A61B 8/468
See application file for complete search history.

(56) References Cited

U.S. PATENT DOCUMENTS

| 7,766,836 B2 * | 8/2010 | Waki ....................... A61B 8/469 600/443 |
| 9,005,128 B2 * | 4/2015 | Imamura ................ A61B 8/463 600/458 |
| 2008/0246724 A1 * | 10/2008 | Pan ......................... G16H 30/20 345/157 |
| 2009/0270733 A1 * | 10/2009 | Koide .................... G01S 15/894 600/458 |
| 2020/0294226 A1 * | 9/2020 | Fujihara .............. G01S 7/52073 |

* cited by examiner

*Primary Examiner* — Shefali D Goradia
(74) *Attorney, Agent, or Firm* — McAndrews, Held & Malloy, Ltd.; Jacob Groethe; David Bates

(57) ABSTRACT

A system and method for transposing markers added to a first ultrasound imaging mode dataset to a second ultrasound imaging mode dataset is provided. The method includes acquiring a first ultrasound image dataset according to a first mode. The method includes processing the first ultrasound image dataset according to the first mode to generate a first mode image. The method includes causing a display system to present the first mode image. The method includes adding at least one marker to the first mode image in response to a user input. The method includes receiving a selection to switch to a second mode. The method includes causing the display system to present a second mode image having the at least one marker added to the first mode image.

17 Claims, 5 Drawing Sheets

METHOD AND SYSTEM FOR TRANSPOSING MARKERS ADDED TO A FIRST ULTRASOUND IMAGING MODE DATASET TO A SECOND ULTRASOUND IMAGING MODE DATASET

FIELD

Certain embodiments relate to ultrasound imaging. More specifically, certain embodiments relate to a method and system for transposing markers added to a first ultrasound imaging mode dataset to a second ultrasound imaging mode dataset.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Three-dimensional (3D) and/or four-dimensional (4D) ultrasound datasets provide a comprehensive overview of an anatomical structure of interest. For example, a 3D rendered view of a mitral valve of a heart may allow an ultrasound operator to easily identify a plane of the coaptation of the leaflets. The ultrasound operator may position markers at coaptation landmark points in the identified plane and a plane perpendicular to the identified plane that may be used, for example, to deploy an artificial mitral valve. The markers are viewable at a same location with respect to the ultrasound probe irrespective of the view and/or views presented (e.g., rotated 3D renderings, cropped 3D renderings, slices of the 3D dataset that intersect the marker, etc.). However, 3D and/or 4D ultrasound datasets suffer from lower spatial and temporal resolutions than 2D and/or biplane ultrasound datasets because the frame rate in 3D and/or 4D ultrasound modes is usually much lower than in 2D ultrasound modes, resulting in the physical resolution of an image plane being much lower. Accordingly, ultrasound operators often prefer to switch from viewing 3D and/or 4D image datasets to acquiring and displaying 2D and/or biplane ultrasound images during the critical guidance phase of deploying the artificial mitral valve. However, markers added to 3D and/or 4D ultrasound datasets are not available in acquired 2D and/or biplane ultrasound datasets. Similarly, markers added to 2D and/or biplane ultrasound datasets are not available in 3D and/or 4D ultrasound datasets.

Moreover, in some cases, an ultrasound operator may desire to manipulate an ultrasound probe to obtain 2D and/or biplane views that intersect three or more markers added to a 3D and/or 4D ultrasound dataset. However, the appropriate manipulation of the ultrasound probe may be difficult to determine, particularly for less experienced ultrasound operators.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for transposing markers added to a first ultrasound imaging mode dataset to a second ultrasound imaging mode dataset, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
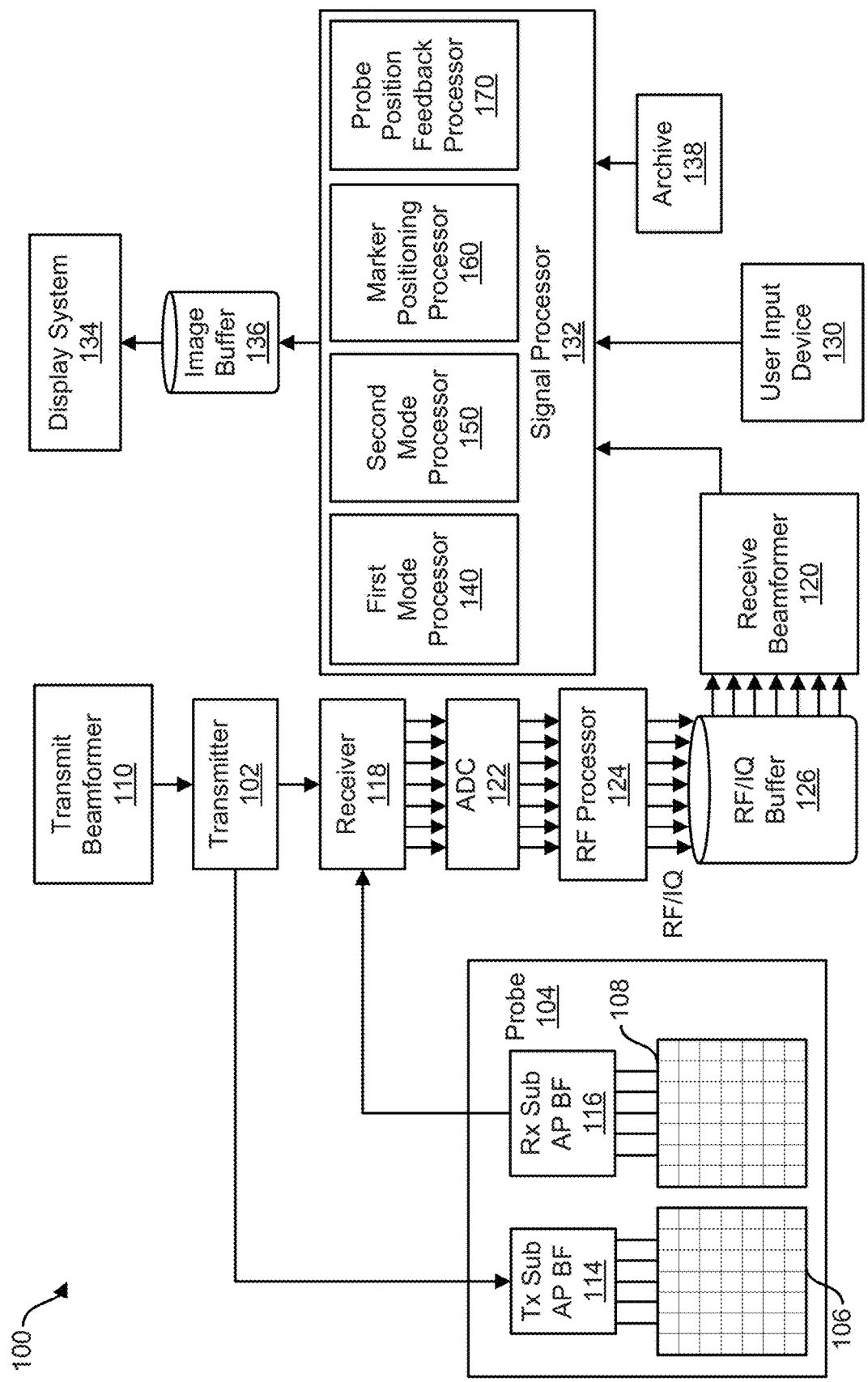
FIG. 1 is a block diagram of an exemplary ultrasound system that is operable to transpose markers added to a first ultrasound imaging mode dataset to a second ultrasound imaging mode dataset, in accordance with various embodiments.

Certain embodiments may be found in a method and system for transposing markers added to a first ultrasound imaging mode dataset to a second ultrasound imaging mode dataset. For example, aspects of the present disclosure have the technical effect of acquiring a 2D ultrasound image dataset based on locations of markers added to a 3D ultrasound image dataset and presenting the 2D ultrasound image dataset with the markers transposed from the 3D ultrasound image dataset. Moreover, aspects of the present disclosure have the technical effect of transposing markers added to a 2D ultrasound image dataset to a 3D ultrasound image dataset. Furthermore, aspects of the present disclosure have the technical effect of providing probe position feedback based on locations of markers in a 3D ultrasound image dataset to guide an ultrasound operator in manipulating an ultrasound probe to a position to acquire a 2D ultrasound image dataset intersecting the marker locations.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), three-dimensional (3D) mode, 3D Zoom mode (e.g., thin slab), M-mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to transpose markers added to a first ultrasound imaging mode dataset to a second ultrasound imaging mode dataset, in accordance with various embodiments. Referring to FIG. 1, there is shown an ultrasound system 100 comprising a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two-dimensional (2D) array of piezoelectric elements. In various embodiments, the ultrasound probe 104 may be a matrix array transducer or any suitable transducer operable to acquire 2D and/or 3D (including 4D) ultrasound image datasets. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a heart, a fetus, a lung, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or a plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, image acquisition and scan parameters, settings, configuration parameters, select protocols and/or templates, change scan mode, add markers to displayed ultrasound images, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, graphic processing units, microprocessors, microcontrollers, and/or the like. The signal processor 132 may be an integrated component, or may be distributed across various locations, for example. In an exemplary embodiment, the signal processor 132 may comprise a first mode processor 140, a second mode processor 150, a marker positioning processor 160 and a probe position feedback processor 170 may be capable of receiving input information from a user input device 130 and/or archive 138, generating an output displayable by a display system 134, and manipulating the output in response to input information from a user input device 130, among other things. The signal processor 132, first mode processor 140, second mode processor 150, marker positioning processor 160 and probe position feedback processor 170 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a first mode processor 140 that comprises suitable logic, circuitry, interfaces and/or code that may be operable to process an acquired and/or retrieved first mode ultrasound image dataset to generate ultrasound images according to a first mode. As an example, the first mode may be a 3D mode (e.g., 3D or 4D) and the first mode processor 140 may be configured to process a received first mode ultrasound image dataset into 3D or 4D image(s). For example, the first mode processor 140 may perform multiplanar reformation (MPR) techniques, volume rendering techniques, and/or any suitable 3D.4D processing techniques to generate renderings and/or image slices from the 3D ultrasound image dataset. As another example, the first mode may be a 2D mode (e.g., B-mode, biplane mode, triplane mode, or the like) and the first mode processor 140 may be configured to process a received first mode ultrasound image dataset into 2D image(s). The first mode image(s) may be provided to the marker positioning processor 160, presented at the display system 134 and/or stored at archive 138 or any suitable data storage medium.

The signal processor 132 may include a second mode processor 150 that comprises suitable logic, circuitry, interfaces and/or code that may be operable to process an acquired and/or retrieved second mode ultrasound image dataset to generate ultrasound images according to a second mode different from the first mode. For example, the second mode may be a 2D mode or a 3D Zoom mode when the first mode is a 3D mode. As another example, the second mode may be a 3D mode or a 3D Zoom mode when the first mode is a 2D mode. The first mode image(s) may be provided to the marker positioning processor 160, presented at the display system 134 and/or stored at archive 138 or any suitable data storage medium. In various embodiments, the first mode ultrasound image dataset and the second mode ultrasound image dataset may be acquired by the ultrasound probe 104 provided at a same location. For example, an ultrasound operator operating an ultrasound probe 104 to a desired location may switch between acquiring the first mode ultrasound image dataset and the second mode ultrasound image dataset at the desired location.

The signal processor 132 may include a marker positioning processor 160 that comprises suitable logic, circuitry, interfaces and/or code that may be operable to add one or more markers to first mode ultrasound image(s) based on a user input via the user input device 130. For example, an ultrasound operator may operate a touchscreen, mousing device, trackball, buttons, and/or any suitable user input device 130 to identify locations on the first mode ultrasound image(s). The marker positioning processor 160 may be configured to superimpose a marker, colorize pixels of the first mode ultrasound image data, and/or otherwise mark the selected locations in the first mode ultrasound image data. The markers added to the first mode ultrasound image(s) may comprise location information correlating the marked image location with respect to the ultrasound probe 104. The markers may be colored shapes (e.g., spheres, boxes, stars, etc.), colored highlighting, colorized pixels, labels, and/or any suitable marker. The marker may be placed via the user input device 130 at anatomical landmarks (e.g., coaptation landmark points of leaflets of a mitral valve) or any suitable locations in the first mode ultrasound image(s). The markers and/or the first mode ultrasound image(s) having the markers may be presented at display system 134 and/or stored at archive 138 and/or any suitable data storage medium.

The marker positioning processor 160 may comprise suitable logic, circuitry, interfaces and/or code that may be operable to transpose markers from a first mode ultrasound image dataset to a second mode ultrasound image dataset. As used herein, the terms "transpose," "transposed," and "transposing" refer to the marker position processor 160 automatically adding additional markers to the second mode ultrasound image dataset and/or second mode image, where each of the additional added markers correspond with a marker added to the first mode ultrasound image dataset and/or first mode image in response to a user direction provided via the user input device 130. In this way, the marker positioning processor 160 may utilize the location information with respect to the ultrasound probe 104 that is associated with each marker in the first ultrasound image dataset to add each additional marker at a corresponding location in the second ultrasound image dataset. For example, an ultrasound operator may acquire a 2D ultrasound image dataset and add markers to the 2D ultrasound image(s) presented at the display system 134. The ultrasound operator may switch to a 3D mode to acquire a 3D/4D or 3D Zoom ultrasound image dataset. The marker positioning processor 160 adds markers to the 3D/4D or 3D Zoom ultrasound image(s) presented at the display system 134 based on the location of the markers in the 2D ultrasound image dataset with respect to the ultrasound probe 104. As another example, the ultrasound operator may acquire a 3D/4D ultrasound image dataset and add markers to the 3D/4D ultrasound image(s) presented at the display system 134. The ultrasound operator may switch to a 2D mode to acquire a 2D ultrasound image dataset or a 3D Zoom mode having a higher framerate and/or greater image quality due in part to the reduced amount of ultrasound image data acquired. The marker positioning processor 160 adds markers to the 2D ultrasound image(s) and/or thin slab image(s) presented at the display system 134 based on the location of the markers in the 3D/4D ultrasound image dataset with respect to the ultrasound probe 104. In various embodiments, if a second mode ultrasound image dataset is a 2D dataset or a 3D zoom dataset and the markers added to the first 3D mode ultrasound image dataset are not in the plane of the 2D ultrasound image dataset or 3D zoom dataset subsequently acquired, the markers may not be shown or the marker positioning processor 160 may provide a visual clue (e.g., smaller marker or different color) to indicate the marker is close to the currently acquired 2D plane or thin slab (e.g., either in front or behind). The transposed markers and/or the second mode ultrasound image(s) having the transposed markers may be presented at display system 134 and/or stored at archive 138 and/or any suitable data storage medium.

In an exemplary embodiment, the marker positioning processor 160 may comprise suitable logic, circuitry, interfaces and/or code that may be operable to provide marker location feedback to the signal processor 132 to control acquisition of the second mode ultrasound image dataset based on the marker location information. For example, an ultrasound operator may acquire a 3D/4D ultrasound image dataset and add markers to the 3D/4D ultrasound image(s) presented at the display system 134. The ultrasound operator may switch to a 2D mode to acquire a 2D ultrasound image dataset or to a 3D zoom mode to acquire thin slab image(s). The marker position processor 160 may be configured to provide the signal processor 132 marker location feedback such that the signal processor may control operation of the transmitter 102, the transmit beamformer 110, the ultrasound probe 104, and/or the like to acquire thin slab image(s) or a 2D ultrasound image dataset having one or more planes (e.g., B-mode, biplane, triplane) that intersect the markers added to the 3D/4D ultrasound image dataset. For example, if an ultrasound operator adds four (4) markers to a 3D/4D ultrasound image dataset and switches to a 2D biplane mode, the signal processor 132 may compute the location of two planes each intersecting a pair of the markers added to the 3D/4D ultrasound image dataset based on the marker location feedback. In various embodiments, the signal processor 132 may use the marker location information to determine the location (e.g., rotation angle and tilt) as well as a depth, width, and the like of 2D ultrasound image dataset or thin slab image(s) to be acquired. In this way, the second 2D mode ultrasound image dataset or thin slab image(s) may be acquired based on the location of the markers added to the first 3D mode ultrasound image dataset.

As another example, an ultrasound operator may acquire a 2D ultrasound image dataset and add markers to the 2D ultrasound image(s) presented at the display system 134. The ultrasound operator may switch to a 3D or 3D Zoom mode to acquire a 3D or 3D Zoom ultrasound image dataset. The marker position processor 160 may be configured to provide the signal processor 132 marker location feedback such that the signal processor may control operation of the transmitter 102, the transmit beamformer 110, the ultrasound probe 104, and/or the like to acquire a 3D or 3D zoom ultrasound image dataset that include the markers added to the 2D ultrasound image dataset. For example, if an ultrasound operator adds four (4) markers to a 2D ultrasound image dataset and switches to a 3D or 3D Zoom mode, the signal processor 132 may place a box defining the 3D ultrasound image dataset acquisition around the markers added to the 2D ultrasound image dataset based on the marker location feedback. In various embodiments, the signal processor 132 may use the marker location information to determine the 3D or 3D Zoom ultrasound image dataset to be acquired and to determine the MPR to be presented (e.g., slices or slabs intersecting the markers) such that the markers are visible in the 3D rendering and MPR. In this way, the second 3D mode ultrasound image dataset or thin slab image(s) may be acquired based on the location of the markers added to the first 2D mode ultrasound image dataset.

Figure 2:
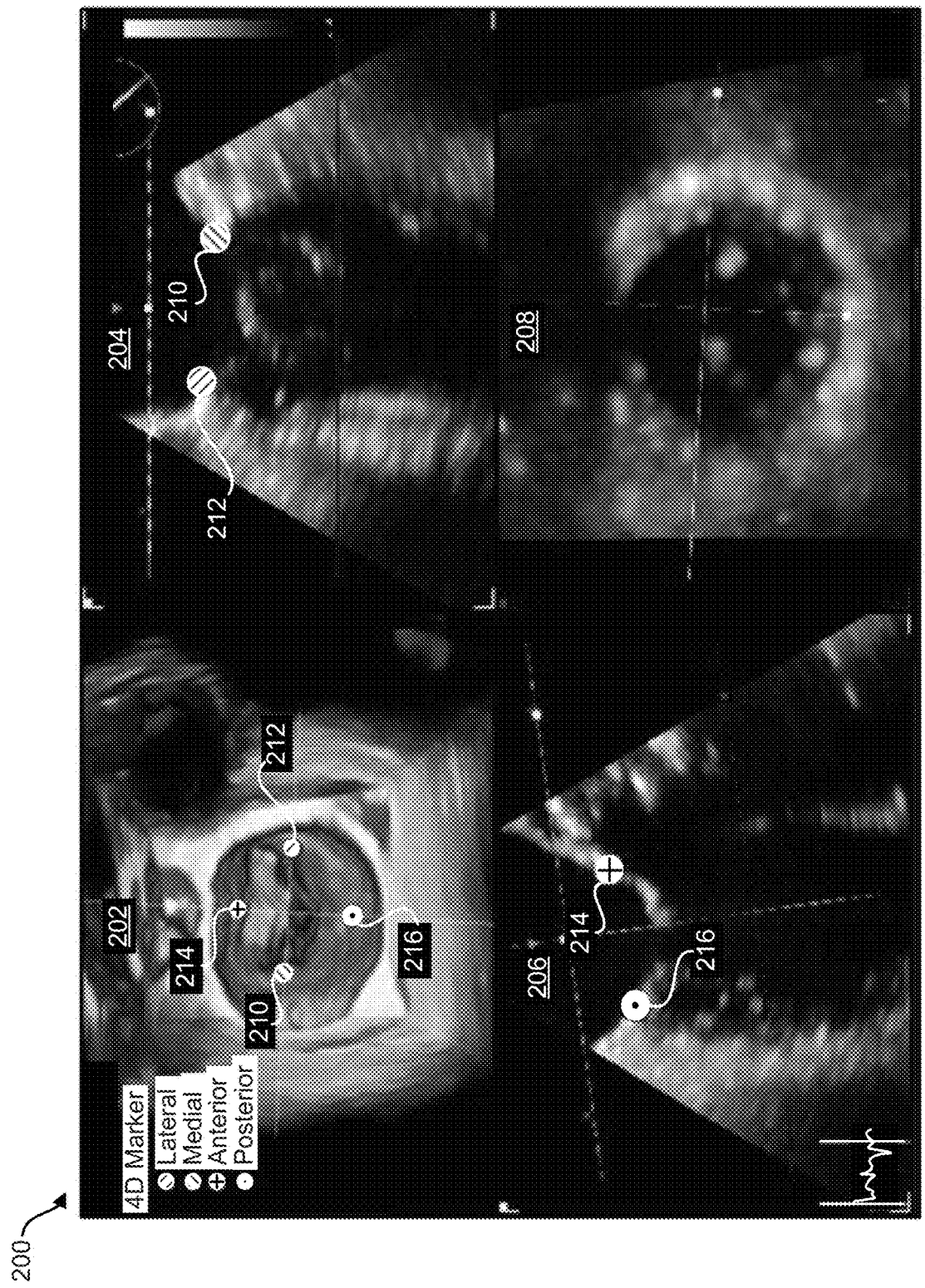
FIG. 2 illustrates a screenshot of an exemplary multiplanar reformation (MPR) of a three-dimensional (3D) ultrasound image dataset having markers identifying landmarks in an anatomical structure, in accordance with various embodiments.

FIG. 2 illustrates a screenshot 200 of an exemplary multiplanar reformation (MPR) 202-208 of a three-dimensional (3D) ultrasound image dataset having markers 210-

216 identifying landmarks in an anatomical structure, in accordance with various embodiments. Referring to FIG. 2, the screenshot 200 of the MPR of the 3D ultrasound image dataset includes a rendered image 202 and three slices 204-208 of the 3D ultrasound image dataset. The three slices may be default slices including a slice 204 along the X-axis, a slice 206 along the Y-axis, and a slice along the Z-axis of the 3D ultrasound image dataset, for example. Additionally and/or alternatively, an ultrasound operator may select the slices for presentation at the display system 134. Additionally and/or alternatively, the signal processor 132 may select the slices for presentation at the display system 134 based on marker location information from markers added via a user input device 130 to a 2D mode ultrasound image dataset, such as the markers 310-316 added to the biplane images 302, 304 of FIG. 3 as described below. The marker position processor 160 may add markers 210-216 to one or more of the MPR images 202-208 as directed via a user input device 130. The marker positioning processor 160 may be configured to automatically transpose markers 210-216 added to locations in the rendered image 202 and/or slices 204-208 to corresponding locations in the appropriate slices 204-208 and/or rendered image 202. For example, the marker positioning processor 160 may automatically add markers 210, 212 to X-plane slice 204 and markers 214, 216 to Y-plane slice 206 in response to markers 210-216 added via the user input device 130 at locations in the rendered image 202. As another example, the marker positioning processor 160 may automatically add markers 210-216 to the rendered image 202 in response to markers 210, 212 added via the user input device 130 to the X-plane slice 204 and markers 214, 216 added via the user input device 130 to the Y-plane slice 206. Additionally and/or alternatively, the markers 210-216 added to the MPR images 202-208 may be transposed from markers added via a user input device 130 to a 2D mode ultrasound image dataset, such as the markers 310-316 added to the biplane images 302, 304 of FIG. 3 as described below. The markers 210-216 may be overlaid on one or more of the MPR images 202-208 by the marker positioning processor 160 and/or the marker positioning processor 160 may colorize pixels of the MPR images 202-208. The markers 210-216 added to the MPR images 202-208 may comprise location information correlating the marked image location with respect to the ultrasound probe 104. The markers 210-216 may be colored shapes (e.g., spheres, boxes, stars, etc.), colored highlighting, colorized pixels, labels, and/or any suitable marker. The markers 210-216 may be positioned at anatomical landmarks (e.g., coaptation landmark points of leaflets of a mitral valve) or any suitable locations in the MPR images 202-208. The markers 210-216 and/or the MPR images 202-208 having the markers 210-216 may be presented at display system 134 and/or stored at archive 138 and/or any suitable data storage medium.

Figure 3:
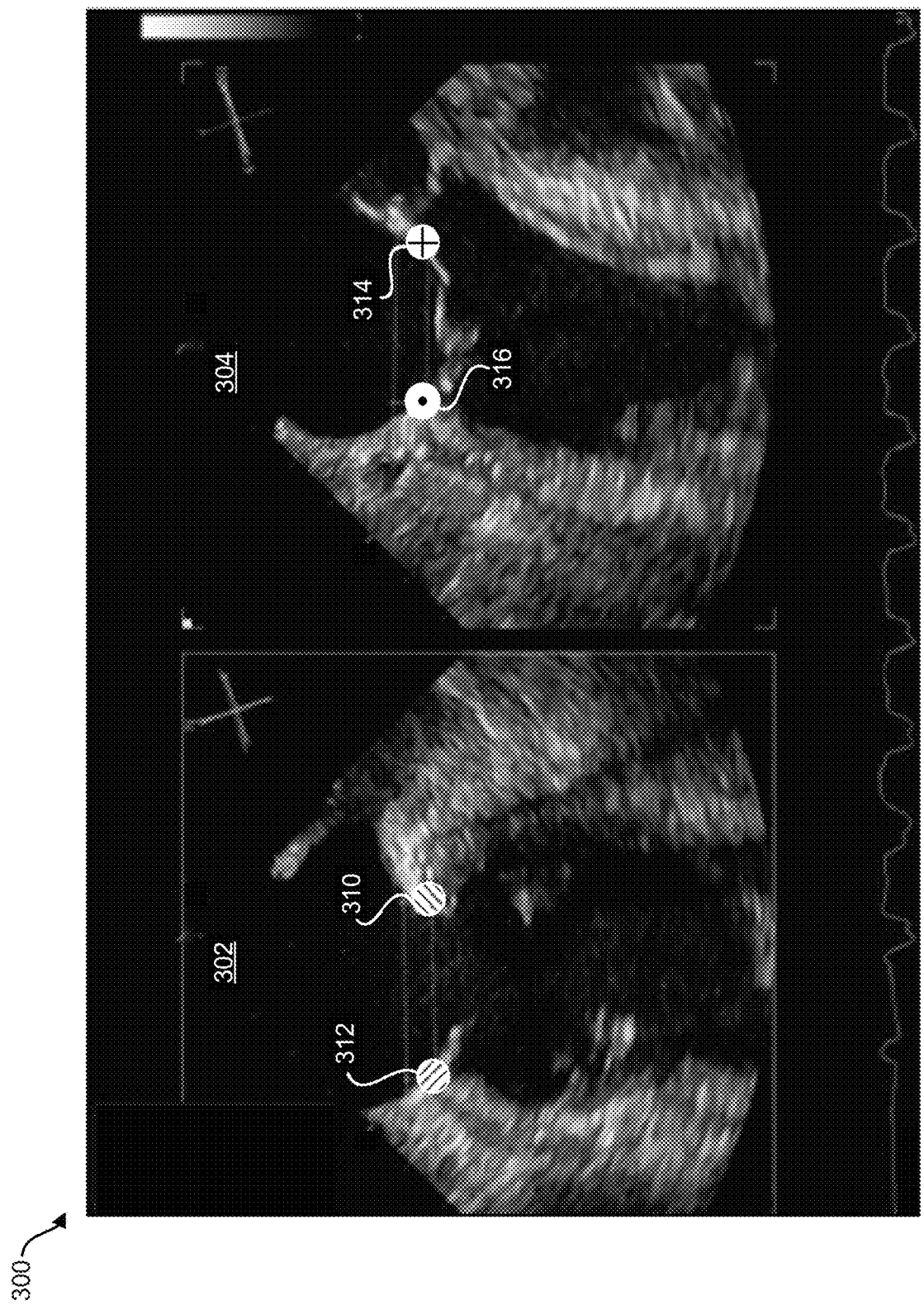
FIG. 3 illustrates a screenshot of an exemplary biplane view of a two-dimensional (2D) ultrasound image dataset having markers identifying landmarks in an anatomical structure, in accordance with various embodiments.

FIG. 3 illustrates a screenshot 300 of an exemplary biplane view 302, 304 of a two-dimensional (2D) ultrasound image dataset having markers 310-316 identifying landmarks in an anatomical structure, in accordance with various embodiments. Referring to FIG. 3, the screenshot 300 of the biplane view 302, 304 of the 2D ultrasound image dataset includes first 302 and second 304 intersecting image slices. The marker position processor 160 may add markers 310-316 to one or more of the biplane images 302, 304 as directed via a user input device 130. Additionally and/or alternatively, the markers 310-316 added to the biplane images 302, 304 may be transposed from markers added via a user input device 130 to a 3D mode ultrasound image dataset, such as the markers 210-216 added to the MPR images 202-208 of FIG. 2. The markers 310-316 may be overlaid on one or more of the biplane images 302, 304 by the marker positioning processor 160 and/or the marker positioning processor 160 may colorize pixels of the biplane images 302, 304. The markers 310-316 added to the biplane images 302, 304 may comprise location information correlating the marked image location with respect to the ultrasound probe 104. The markers 310-316 may be colored shapes (e.g., spheres, boxes, stars, etc.), colored highlighting, colorized pixels, labels, and/or any suitable marker. The markers 310-316 may be positioned at anatomical landmarks (e.g., coaptation landmark points of leaflets of a mitral valve) or any suitable locations in the biplane images 302, 304. The markers 310-316 and/or the biplane images 302, 304 having the markers 310-316 may be presented at display system 134 and/or stored at archive 138 and/or any suitable data storage medium.

Referring again to FIG. 1, the probe position feedback processor 170 may be configured to present ultrasound probe position feedback at the display system 134 based on marker location information for guiding the manipulation of the ultrasound probe 104 to a position for obtaining one or more ultrasound images intersecting markers added to the displayed first mode ultrasound image(s) and/or second mode ultrasound image(s). For example, the probe position feedback processor 170 may be configured to provide probe position feedback based on locations of markers in a 3D ultrasound image dataset to guide an ultrasound operator in manipulating an ultrasound probe to a position to acquire a 2D ultrasound image dataset intersecting the markers. The position feedback may be visual feedback, audio feedback, and/or physical feedback. The visual feedback may be a visual indicator presented at the display system 134 or any suitable visual feedback. For example, the visual feedback may include navigation arrows, textual navigation instructions, or the like. The audible feedback may be audible navigation instructions or any suitable audible feedback. The physical feedback may include causing the probe 104 to vibrate at locations indicating probe movement directions or any suitable physical feedback. The probe position feedback processor 170 may be configured to continuously update the probe position feedback until the ultrasound probe 104 is correctly positioned to obtain the ultrasound image dataset intersecting the markers.

Figure 4:
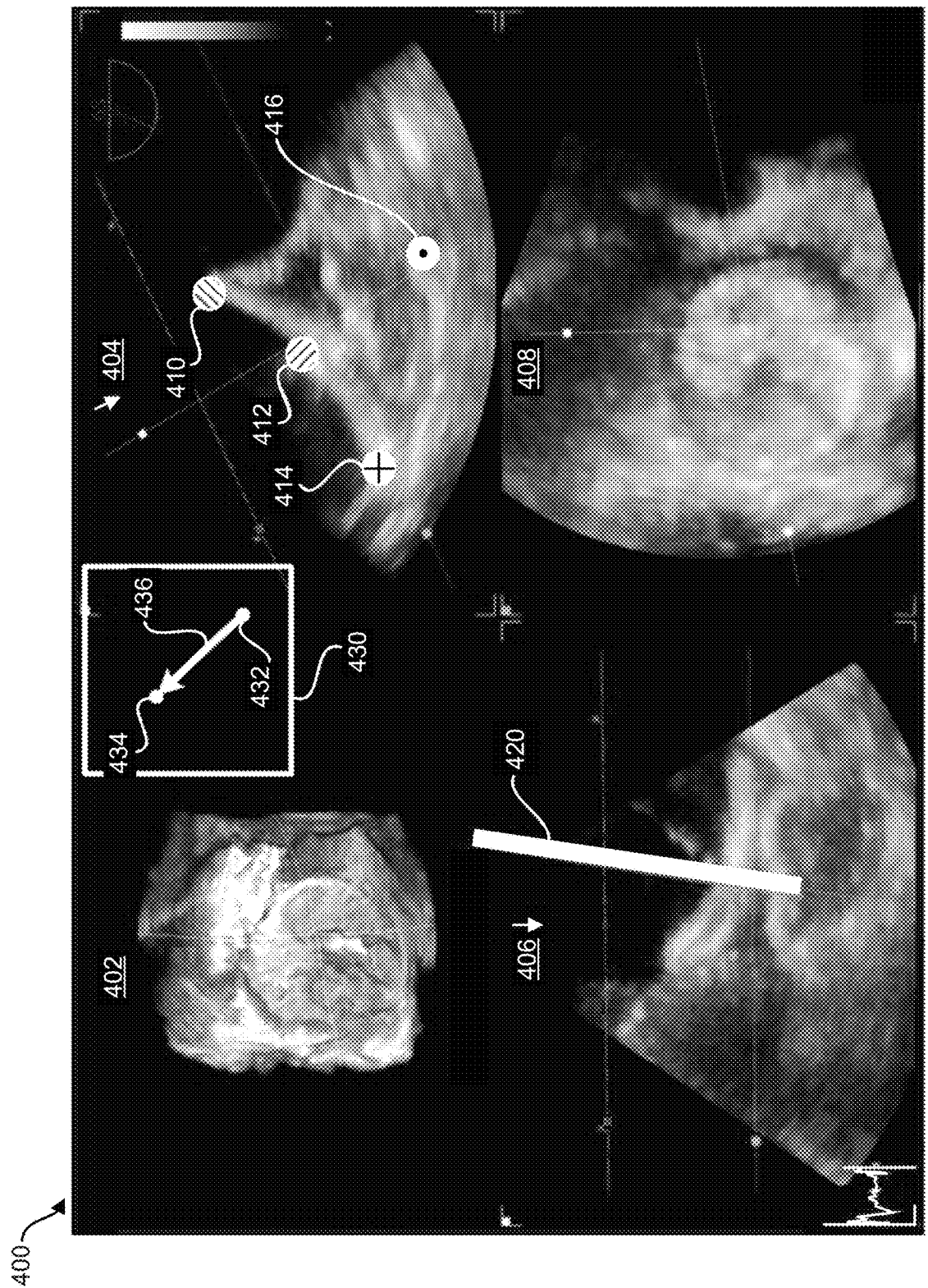
FIG. 4 illustrates a screenshot of an exemplary MPR of a 3D ultrasound image dataset having markers identifying landmarks in an anatomical structure and a probe position feedback indicator to guide an operator to manipulate an ultrasound probe to obtain a 2D ultrasound image dataset intersecting the marker locations, in accordance with various embodiments.

FIG. 4 illustrates a screenshot 400 of an exemplary MPR 402-408 of a 3D ultrasound image dataset having markers 410-416 identifying landmarks in an anatomical structure and a probe position feedback indicator 430 to guide an operator to manipulate an ultrasound probe 104 to obtain a 2D ultrasound image dataset intersecting the marker locations, in accordance with various embodiments. Referring to FIG. 4, the screenshot 400 of the MPR of the 3D ultrasound image dataset includes a rendered image 402 and slices 404-408 of the 3D ultrasound image dataset. The slices may be default slices including a slice 404 along the X-axis, a slice 406 along the Y-axis, and a slice 408 along the Z-axis of the 3D ultrasound image dataset, for example. Additionally and/or alternatively, an ultrasound operator may select the slices for presentation at the display system 134. The marker position processor 160 may add markers 410-416 to one or more of the MPR images 402-408 as directed via a user input device 130. The markers 410-416 may be overlaid on one or more of the MPR images 402-408 by the marker positioning processor 160 and/or the marker positioning processor 160 may colorize pixels of the MPR images 402-408. The markers 410-416 added to the MPR images 402-408 may comprise location information correlating the marked image location with respect to the ultrasound probe 104. The markers 410-416 may be colored shapes (e.g., spheres, boxes, stars, etc.), colored highlighting, colorized pixels, labels, and/or any suitable marker. The markers 410-416 may be positioned at anatomical landmarks (e.g., coaptation landmark points of leaflets of a mitral valve) or any suitable locations in the MPR images 402-408. The markers 410-416 and/or the MPR images 402-408 having the markers 410-416 may be presented at display system 134 and/or stored at archive 138 and/or any suitable data storage medium.

In various embodiments, a 2D mode ultrasound image dataset intersecting the markers 410-416 in the MPR images 402-408 may not be obtainable at a current ultrasound probe position 420. In such cases, the probe position feedback processor 170 may be configured to provide probe position feedback 430 based on locations of markers 410-416 in the MPR images 402-408 to guide an ultrasound operator in manipulating the ultrasound probe 104 to a position to acquire a 2D ultrasound image dataset intersecting the markers 410-416. The position feedback may be visual feedback as shown in FIG. 4 and/or may include audio feedback and/or physical feedback. The visual feedback may be a visual indicator 430 presented at the display system 134 or any suitable visual feedback. The probe position visual indicator 430 may identify a current probe location 432, an end location 434 to obtain the 2D ultrasound image dataset intersecting the markers 410-416, a distance indicator 436 illustrating an amount of probe movement to move from the current probe location 432 to the end location 434, and the like. In an exemplary embodiment, the probe position visual indicator 430 may additionally and/or alternatively provide probe orientation indicators to provide instructions for tilting the probe 104, rotating the probe 104, and/or the like. In certain embodiments, the visual feedback may additionally and/or alternatively include textual navigation instructions or the like. The probe position feedback processor 170 may be configured to continuously update the probe position feedback 430 until the ultrasound probe 104 is correctly positioned to obtain the ultrasound image dataset intersecting the markers. As an example, the navigational arrow 436 (also referred to as a distance indicator) may shorten as the probe 104 is moved toward the end location 434 and may grow longer if the probe 104 is moved away from the end location 434. The direction of the navigational arrow 436 may also be updated based on the probe 104 movement.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present 2D ultrasound image datasets 302, 304, 3D ultrasound image datasets 202-208, 402-408, markings 210-216, 310-316, 410-416, probe position feedback 430, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores first mode ultrasound image datasets (e.g., 3D images 202-208, 402-408), markings 210-216, 410-416 and/or first mode images having markings 210-216, 410-416, second mode ultrasound image datasets (e.g., 2D images 302, 304), markings 310-316 and/or second mode images having markings 310-316, instructions for processing received ultrasound image datasets according to a first mode, instructions for processing received ultrasound image datasets according to a second mode, instructions for positioning and/or transposing markers 210-216, 310-316, 410-416 in ultrasound images 202-208, 302-304, 402-408, instructions for providing ultrasound image acquisition instructions for obtaining a 2D ultrasound image dataset intersecting markers 210-216 added to a 3D ultrasound image dataset, and/or instructions for providing probe position feedback to manipulate an ultrasound probe 104 to a position for obtaining a 2D ultrasound image dataset intersecting markers 410-416 added to a 3D ultrasound image dataset, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 5:
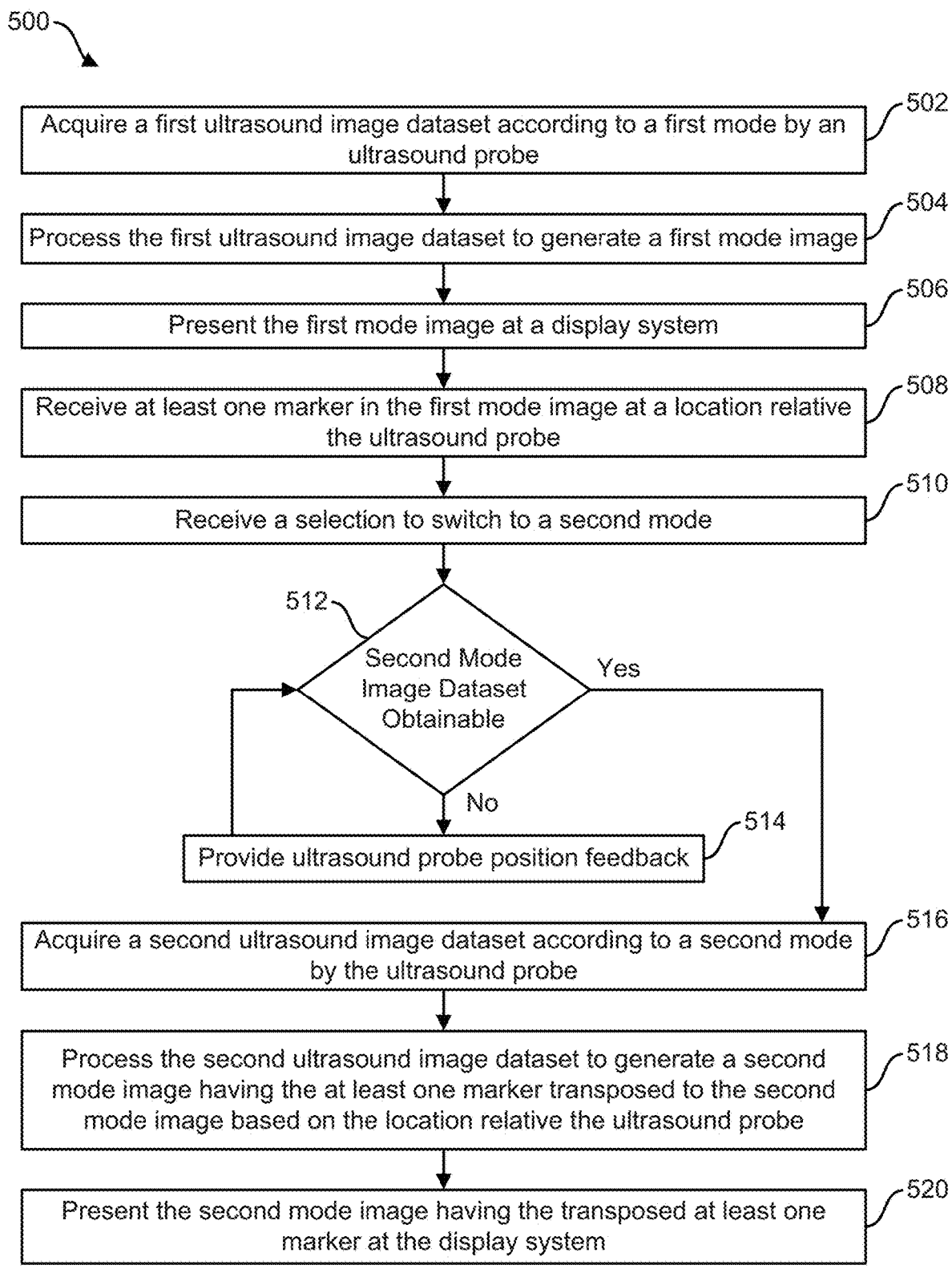
FIG. 5 is a flow chart illustrating exemplary steps that may be utilized for transposing markers added to a first ultrasound imaging mode dataset to a second ultrasound imaging mode dataset, in accordance with various embodiments.

FIG. 5 is a flow chart 500 illustrating exemplary steps 502-520 that may be utilized for transposing markers 210-216, 310-316 added to a first ultrasound imaging mode dataset 202-208, 302-304 to a second ultrasound imaging mode dataset 202-208, 302-304, in accordance with various embodiments. Referring to FIG. 5, there is shown a flow chart 500 comprising exemplary steps 502 through 520. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 502, an ultrasound system 100 may acquire a first ultrasound image dataset according to a first mode. For example, an ultrasound probe 104 in the ultrasound system 100 may be operable to perform an ultrasound scan of a region of interest, such as a mitral valve of a heart. In various embodiments, the ultrasound probe 104 may be a matrix array transducer or any suitable transducer operable to acquire 2D and/or 3D (including 4D) ultrasound image datasets. The ultrasound scan may be performed according to the first mode, such as a 2D mode, 3D mode, or any suitable image acquisition mode. The first ultrasound image dataset may be received by the signal processor 132 and/or stored to archive 138 or any suitable data storage medium from which the signal processor 132 may retrieve the first ultrasound image dataset.

At step 504, the signal processor 132 of the ultrasound system 100 may process the first ultrasound image dataset to generate a first mode image. For example, a first mode processor 140 of the signal processor 132 of the ultrasound system 100 may be configured to process the acquired and/or retrieved first mode ultrasound image dataset to generate ultrasound images according to the first mode. As an example, the first mode may be a 3D mode (e.g., 3D or 4D) and the first mode processor 140 may be configured to process a received first mode ultrasound image dataset into 3D or 4D image(s). For example, the first mode processor 140 may perform multiplanar reformation (MPR) techniques, volume rendering techniques, and/or any suitable 3D/4D processing techniques to generate renderings 202, 402 and/or image slices 204-208, 404-408 from the 3D ultrasound image dataset. As another example, the first mode may be a 2D mode (e.g., B-mode, biplane mode, triplane mode, or the like) and the first mode processor 140 may be configured to process a received first mode ultrasound image dataset into 2D image(s) 302, 304.

At step 506, a display system 134 of the ultrasound system 100 may present the first mode image. For example, the first mode processor 140 may be configured to cause the display system 134 to present the first mode image(s) generated at step 504.

At step 508, the first mode image 202-208, 302-304, 402-408 may receive at least one marker 210-216, 310-316, 410-416 at a location relative the ultrasound probe 104. For example, a marker positioning processor 160 of the signal processor 132 of the ultrasound system 100 may be configured to add one or more markers 210-216, 310-316, 410-416 to first mode image(s) 202-208, 302-304, 402-408 based on a user input via the user input device 130. As an example, an ultrasound operator may operate a touchscreen, mousing device, trackball, buttons, and/or any suitable user input device 130 to identify locations on the first mode image(s) 202-208, 302-304, 402-408. The marker positioning processor 160 may be configured to superimpose a marker 210-216, 310-316, 410-416, colorize pixels of the first mode ultrasound image data, and/or otherwise mark the selected locations in the first mode ultrasound image dataset. The markers 210-216, 310-316, 410-416 added to the first mode image(s) 202-208, 302-304, 402-408 may comprise location information correlating the marked image location with respect to the ultrasound probe 104. The markers 210-216, 310-316, 410-416 may be colored shapes (e.g., spheres, boxes, stars, etc.), colored highlighting, colorized pixels, labels, and/or any suitable marker. The markers 210-216, 310-316, 410-416 may be placed via the user input device 130 at anatomical landmarks (e.g., coaptation landmark points of leaflets of a mitral valve) or any suitable locations in the first mode image(s) 202-208, 302-304, 402-408.

At step 510, the signal processor 132 of the ultrasound system 100 may receive a selection to switch to a second mode. For example, the signal processor 132 may receive a user directive to switch from acquiring and displaying a 3D mode ultrasound image dataset to acquiring and displaying a 2D mode ultrasound image dataset or thin slab image(s) (3D Zoom mode) via a user input device 130. As another example, the signal processor 132 may receive a user directive to switch from acquiring and displaying a 2D mode ultrasound image dataset to acquiring and displaying a 3D or 3D Zoom mode ultrasound image dataset via a user input device 130.

At step 512, a signal processor 132 of the ultrasound system 100 may determine whether a second mode ultrasound image dataset is obtainable at a current ultrasound probe position. For example, a probe position feedback processor 170 may be configured to determine whether a 2D ultrasound image dataset 302, 304 intersecting markers 210-216, 410-416 added to a 3D ultrasound image dataset 202-208, 402-408 is obtainable based on marker location information and a current ultrasound probe position. The method 500 may proceed to step 514 if the second mode ultrasound image dataset 302, 304 intersecting the markers 210-216, 410-416 added to the first ultrasound image dataset 202-208, 402-408 is not obtainable at a current ultrasound probe position. The method 500 may proceed to step 516 once the ultrasound probe 104 is in a position to obtain the second mode ultrasound image dataset 302, 304 intersecting the markers 210-216, 410-416 added to the first ultrasound image dataset 202-208, 402-408. In various embodiments, the probe position feedback processor 170 may provide an indication as to whether the second mode ultrasound image dataset is obtainable prior to step 510 such that an ultrasound operator is aware whether ultrasound probe manipulation is needed prior to selecting to switch to the second mode at step 510. For example, the indication may be a visual icon and/or message presented at the display system 134.

At step 514, the signal processor 132 may provide ultrasound probe position feedback 430 if the second mode ultrasound image dataset 302, 304 intersecting the markers 210-216, 410-416 added to the first ultrasound image dataset 202-208, 402-408 is not obtainable at a current ultrasound probe position. For example, the probe position feedback processor 170 of the signal processor 132 may be configured to provide probe position feedback 430 based on locations of markers 210-216, 410-416 in the 3D ultrasound images 202-208, 402-408 to guide an ultrasound operator in manipulating the ultrasound probe 104 to a position to acquire a 2D ultrasound image dataset 302, 304 or thin slab image(s) intersecting the markers 210-216, 410-416. The position feedback 430 may be visual feedback 430, audio feedback, and/or physical feedback. The visual feedback may be a visual indicator 430 presented at the display system 134 or any suitable visual probe navigation feedback. The audible feedback may be audible navigation instructions or any suitable audible feedback. The physical feedback may include causing the probe 104 to vibrate at locations indicating probe movement directions or any suitable physical feedback. The probe position feedback processor 170 may be configured to continuously update the probe position feedback 430 until the ultrasound probe 104 is correctly positioned to obtain the ultrasound image dataset intersecting the markers.

At step 516, the ultrasound system 100 may be configured to acquire a second ultrasound image dataset according to a second mode. For example, an ultrasound probe 104 in the ultrasound system 100 may be operable to switch from a first image acquisition mode to a second image acquisition mode, different from the first mode, in response to the selection to switch to the second mode at step 510. As an example, the ultrasound system 100 may switch from a first 3D mode to a second 2D mode or a second 3D Zoom mode. As another example, the ultrasound system 100 may switch from a first 2D mode to a second 3D or 3D Zoom mode. In a representative embodiment, the marker positioning processor 160 may be configured to provide marker location feedback to the signal processor 132 to control acquisition of the second mode ultrasound image dataset based on the marker location information of the markers 210-216, 310-316, 410-416 added at step 508. For example, when the first mode image is a 3D ultrasound image dataset, the marker position processor 160 may be configured to provide the signal processor 132 marker location feedback such that the signal processor 132 may control operation of the transmitter 102, the transmit beamformer 110, the ultrasound probe 104, and/or the like to acquire a second 3D Zoom mode thin slab image(s) or a second 2D mode ultrasound image dataset having one or more planes (e.g., B-mode, biplane, triplane)

302, 304 that intersect the markers 210-216, 410-416 added to the first 3D mode ultrasound image dataset 202-208, 402-408. In this way, the second 2D mode ultrasound image dataset 302, 304 or the second 3D Zoom mode thin slab image(s) may be acquired based on the location of the markers 210-216, 410-416 added to the first 3D mode ultrasound image dataset 202-208, 402-408. As another example, when the first mode image is a 2D ultrasound image dataset, the marker position processor 160 may be configured to provide the signal processor 132 marker location feedback such that the signal processor 132 may control operation of the transmitter 102, the transmit beamformer 110, the ultrasound probe 104, and/or the like to acquire a 3D or 3D zoom ultrasound image dataset that include the markers added to the 2D ultrasound image dataset. In this way, the second 3D mode ultrasound image dataset or thin slab image(s) may be acquired based on the location of the markers added to the first 2D mode ultrasound image dataset. In various embodiments, the position of the ultrasound probe 104 when acquiring the first ultrasound image dataset according to the first mode at step 502 is the same as the position of the ultrasound probe 104 when acquiring the second ultrasound image dataset according to the second mode at step 516. The second ultrasound image dataset may be received by the signal processor 132 and/or stored to archive 138 or any suitable data storage medium from which the signal processor 132 may retrieve the second ultrasound image dataset.

At step 518, the signal processor 132 may process the second ultrasound image dataset to generate a second mode image having the at least one marker transposed to the second mode image based on the location relative the ultrasound probe 104. For example, a second mode processor 150 of the signal processor 132 of the ultrasound system 100 may be configured to process the acquired and/or retrieved second mode ultrasound image dataset to generate ultrasound images according to the second mode. As an example, the second mode may be a 2D mode (e.g., B-mode, biplane mode, triplane mode, or the like) or 3D Zoom mode (e.g., thin slab image(s)) and the second mode processor 150 may be configured to process a received second mode ultrasound image dataset into 2D image(s) 302, 304 or thin slab image(s). As another example, the second mode may be a 3D mode (e.g., 3D or 4D) or 3D Zoom mode (e.g., thin slab image(s)) and the second mode processor 150 may be configured to process a received second mode ultrasound image dataset into 3D, 4D, or thin slab image(s). For example, the second mode processor 140 may perform multiplanar reformation (MPR) techniques, volume rendering techniques, and/or any suitable 3D/4D or 3D Zoom processing techniques to generate renderings 202, 402, image slices 204-208, 404-408, and/or thin slab image(s) from the 3D or 3D Zoom ultrasound image dataset.

The marker positioning processor 160 may be configured to transpose markers from the first mode ultrasound image dataset to the second mode ultrasound image dataset. The marker positioning processor 160 may utilize the location information with respect to the ultrasound probe 104 that is associated with each marker in the first ultrasound image dataset to add each marker at a corresponding location in the second ultrasound image dataset. For example, the marker positioning processor 160 may add markers to the second 3D mode ultrasound image(s) presented at the display system 134 based on the location of the markers in the first 2D mode ultrasound image dataset with respect to the ultrasound probe 104. As another example, the marker positioning processor 160 may add markers to the second 2D mode ultrasound image(s) presented at the display system 134 based on the location of the markers in the first 3D mode ultrasound image dataset with respect to the ultrasound probe 104. In various embodiments, if a second mode ultrasound image dataset is a 2D dataset 302, 304 and the markers 210-216, 410-416 added to the first 3D mode ultrasound image dataset 202-208, 402-408 at step 508 are not in the plane of the 2D ultrasound image dataset 302, 304 acquired at step 516, the markers 310-316 may not be shown or the marker positioning processor 160 may provide a visual clue (e.g., smaller marker or different color) to indicate the marker is close to the currently acquired 2D plane (e.g., either in front or behind).

At step 520, the display system 134 may present the second mode image having the transposed at least one marker. For example, the second mode processor 150 and/or the marker positioning processor 160 may be configured to cause the display system 134 to present the second mode image(s) having the transposed markers generated at step 518. In various embodiments, when the first mode image is a 2D ultrasound image dataset, the marker position processor 160 may be configured to provide the signal processor 132 marker location feedback such that the signal processor 132 may select the 3D images views 202-208, 402-408 from the 3D ultrasound image dataset that intersect and/or include the markers 310-316 added to the first 2D mode ultrasound image dataset 302, 304 for presentation at the display system 134.

Aspects of the present disclosure provide a method 500 and system 100 for transposing markers 210-216, 310-316, 410-416 added to a first ultrasound imaging mode dataset to a second ultrasound imaging mode dataset. In accordance with various embodiments, the method 500 may comprise acquiring 502, by an ultrasound probe 104 of an ultrasound system 100, a first ultrasound image dataset according to a first mode. The method 500 may comprise processing 504, by at least one processor 132, 140 of the ultrasound system 100, the first ultrasound image dataset according to the first mode to generate a first mode image 202-208, 302-304, 402-408. The method 500 may comprise causing 506, by the at least one processor 132, 140, a display system 134 to present the first mode image 202-208, 302-304, 402-408. The method 500 may comprise adding 508, by the at least one processor 132, 160, at least one marker 210-216, 310-316, 410-416 to the first mode image 202-208, 302-304, 402-408 in response to a user input. The method 500 may comprise receiving 510, by the at least one processor 132, a selection to switch to a second mode. The method 500 may comprise causing 516-520, by the at least one processor 132, 150, 160, the display system 134 to present a second mode image 202-208, 302-304, 402-408 having the at least one marker 210-216, 310-316, 410-416 added to the first mode image 202-208, 302-304, 402-408.

In an exemplary embodiment, the first mode is a two-dimensional (2D) mode and the second mode is a three-dimensional (3D) mode. In a representative embodiment, the first mode is a 3D mode and the second mode is a 2D mode. In various embodiments, causing 516-520 the display system 134 to present the second mode image 202-208, 302-304, 402-408 having the at least one marker 210-216, 310-316, 410-416 added to the first mode image 202-208, 302-304, 402-408 may comprise acquiring 516, by the ultrasound probe 104, a second ultrasound image dataset according to the second mode. The causing 516-520 the display system 134 to present the second mode image 202-208, 302-304, 402-408 having the at least one marker 210-216, 310-316, 410-416 added to the first mode image 202-208, 302-304, 402-408 may comprise processing 518, by the at least one processor 132, 150, the second ultrasound image dataset according to the second mode to generate the second mode image 202-208, 302-304, 402-408. The causing 516-520 the display system 134 to present the second mode image 202-208, 302-304, 402-408 having the at least one marker 210-216, 310-316, 410-416 added to the first mode image 202-208, 302-304, 402-408 may comprise transposing 518, by the at least one processor 132, 160, the at least one marker 210-216, 310-316, 410-416 from the first mode image 202-208, 302-304, 402-408 to the second mode image 202-208, 302-304, 402-408. In certain embodiments, the first ultrasound image dataset and the second ultrasound image dataset are acquired by the ultrasound probe 104 at a same ultrasound probe position. The at least one marker 210-216, 310-316, 410-416 comprises location information with respect to the ultrasound probe 104. The transposing 518 the at least one marker 210-216, 310-316, 410-416 from the first mode image 202-208, 302-304, 402-408 to the second mode image 202-208, 302-304, 402-408 is based on the location information. In an exemplary embodiment, the acquiring 516 the second ultrasound image dataset is based on the location information of the at least one marker 210-216, 310-316, 410-416 added to the first mode image 202-208, 302-304, 402-408 such that the second mode image 202-208, 302-304, 402-408 one or both of includes or intersects the at least one marker 210-216, 310-316, 410-416 added to the first mode image 202-208, 302-304, 402-408. In a representative embodiment, the at least one marker 210-216, 310-316, 410-416 added to the first mode image 202-208, 302-304, 402-408 comprises at least three markers 210-216, 310-316, 410-416, each of the at least three markers 210-216, 310-316, 410-416 comprising location information with respect to the ultrasound probe 104. The method 500 may further comprise determining 512, by the at least one processor 132, 170, whether the second ultrasound image dataset intersecting the at least three markers 210-216, 310-316, 410-416 added to the first mode image 202-208, 302-304, 402-408 is obtainable. The method 500 may comprise causing 514, by the at least one processor 132, 170, the display system 134 to present probe position feedback 430 based on the location information of each of the at least three markers 210-216, 310-316, 410-416 to guide manipulation of the ultrasound probe 104 to an updated position 434 to acquire the second ultrasound image dataset intersecting the at least three markers 210-216, 310-316, 410-416 added to the first mode image 202-208, 302-304, 402-408.

Various embodiments provide a system 100 for transposing markers added to a first ultrasound imaging mode dataset to a second ultrasound imaging mode dataset. The ultrasound system 100 may comprise an ultrasound probe 104, a display system 134, and at least one processor 132, 140, 150, 160, 170. The ultrasound probe 104 may be operable to acquire a first ultrasound image dataset according to a first mode. The at least one processor 132, 140 may be configured to process the first ultrasound image dataset according to the first mode to generate a first mode image 202-208, 302-304, 402-408. The at least one processor 132, 140 may be configured to cause the display system 134 to present the first mode image 202-208, 302-304, 402-408. The at least one processor 132, 160 may be configured to add at least one marker 210-216, 310-316, 410-416 to the first mode image 202-208, 302-304, 402-408 in response to a user input. The at least one processor 132 may be configured to receive a selection to switch to a second mode. The at least one processor 132, 150, 160 may be configured to cause the display system 134 to present a second mode image 202-208, 302-304, 402-408 having the at least one marker 210-216, 310-316, 410-416 added to the first mode image 202-208, 302-304, 402-408.

In a representative embodiment, the first mode is a 2D mode and the second mode is a 3D mode. In various embodiments, the first mode is a 3D mode and the second mode is a 2D mode. In certain embodiments, the at least processor 132 may be configured to cause the display system 134 to present the second mode image 202-208, 302-304, 402-408 having the at least one marker 210-216, 310-316, 410-416 added to the first mode image 202-208, 302-304, 402-408 by causing the ultrasound probe 104 to acquire a second ultrasound image dataset according to the second mode. The at least processor 132, 150 may be configured to cause the display system 134 to present the second mode image 202-208, 302-304, 402-408 having the at least one marker 210-216, 310-316, 410-416 added to the first mode image 202-208, 302-304, 402-408 by processing the second ultrasound image dataset according to the second mode to generate the second mode image 202-208, 302-304, 402-408. The at least processor 132, 160 may be configured to cause the display system 134 to present the second mode image 202-208, 302-304, 402-408 having the at least one marker 210-216, 310-316, 410-416 added to the first mode image 202-208, 302-304, 402-408 by transposing the at least one marker 210-216, 310-316, 410-416 from the first mode image 202-208, 302-304, 402-408 to the second mode image 202-208, 302-304, 402-408. In an exemplary embodiment, the first ultrasound image dataset and the second ultrasound image dataset are acquired by the ultrasound probe 104 at a same ultrasound probe position. The at least one marker 210-216, 310-316, 410-416 may comprise location information with respect to the ultrasound probe 104. The transposing the at least one marker 210-216, 310-316, 410-416 from the first mode image 202-208, 302-304, 402-408 to the second mode image 202-208, 302-304, 402-408 may be based on the location information. In a representative embodiment, the second ultrasound image dataset may be acquired by the ultrasound probe 104 based on the location information of the at least one marker 210-216, 310-316, 410-416 added to the first mode image 202-208, 302-304, 402-408 such that the second mode image 202-208, 302-304, 402-408 one or both of includes or intersects the at least one marker 210-216, 310-316, 410-416 added to the first mode image 202-208, 302-304, 402-408. In various embodiments, the at least one marker 210-216, 310-316, 410-416 added to the first mode image 202-208, 302-304, 402-408 comprises at least three markers 210-216, 310-316, 410-416, each of the at least three markers 210-216, 310-316, 410-416 comprising location information with respect to the ultrasound probe 104. The at least one processor 132, 170 may be configured to determine whether the second ultrasound image dataset intersecting the at least three markers 210-216, 310-316, 410-416 added to the first mode image 202-208, 302-304, 402-408 is obtainable. The at least one processor 132, 170 may be configured to cause the display system 134 to present probe position feedback 430 based on the location information of each of the at least three markers 210-216, 310-316, 410-416 to guide manipulation of the ultrasound probe 104 to an updated position 434 to acquire the second ultrasound image dataset intersecting the at least three markers 210-216, 310-316, 410-416 added to the first mode image 202-208, 302-304, 402-408.

Certain embodiments provide a non-transitory computer readable medium having stored thereon, a computer program having at least one code section. The at least one code section is executable by a machine for causing the machine to perform steps 500. The steps 500 may comprise receiving 502 a first ultrasound image dataset acquired according to a first mode. The steps 500 may comprise processing 504 the first ultrasound image dataset according to the first mode to generate a first mode image 202-208, 302-304, 402-408. The steps 500 may comprise causing 506 a display system 134 to present the first mode image 202-208, 302-304, 402-408. The steps 500 may comprise adding 508 at least one marker 210-216, 310-316, 410-416 to the first mode image 202-208, 302-304, 402-408 in response to a user input. The steps 500 may comprise receiving 510 a selection to switch to a second mode. The steps 500 may comprise causing 516-520 the display system 134 to present a second mode image 202-208, 302-304, 402-408 having the at least one marker 210-216, 310-316, 410-416 added to the first mode image 202-208, 302-304, 402-408.

In various embodiments, the first mode is a 2D mode and the second mode is a 3D mode. In certain embodiments, the first mode is a 3D mode and the second mode is a 2D mode. In a representative embodiment, causing 516-520 the display system 134 to present the second mode image 202-208, 302-304, 402-408 having the at least one marker 210-216, 310-316, 410-416 added to the first mode image 202-208, 302-304, 402-408 may comprise receiving 516 a second ultrasound image dataset acquired according to the second mode. The causing 516-520 the display system 134 to present the second mode image 202-208, 302-304, 402-408 having the at least one marker 210-216, 310-316, 410-416 added to the first mode image 202-208, 302-304, 402-408 may comprise processing 518 the second ultrasound image dataset according to the second mode to generate the second mode image 202-208, 302-304, 402-408. The causing 516-520 the display system 134 to present the second mode image 202-208, 302-304, 402-408 having the at least one marker 210-216, 310-316, 410-416 added to the first mode image 202-208, 302-304, 402-408 may comprise transposing 518 the at least one marker 210-216, 310-316, 410-416 from the first mode image 202-208, 302-304, 402-408 to the second mode image 202-208, 302-304, 402-408. In an exemplary embodiment, the first ultrasound image dataset and the second ultrasound image dataset are acquired by an ultrasound probe 104 at a same ultrasound probe position. The second ultrasound image dataset may be acquired based on the location information of the at least one marker 210-216, 310-316, 410-416 added to the first mode image 202-208, 302-304, 402-408 such that the second mode image 202-208, 302-304, 402-408 one or both of includes or intersects the at least one marker 210-216, 310-316, 410-416 added to the first mode image 202-208, 302-304, 402-408. The at least one marker 210-216, 310-316, 410-416 may comprise location information with respect to the ultrasound probe 104. The transposing 518 the at least one marker 210-216, 310-316, 410-416 from the first mode image 202-208, 302-304, 402-408 to the second mode image 202-208, 302-304, 402-408 may be based on the location information.

In various embodiments, the at least one marker 210-216, 310-316, 410-416 added to the first mode image 202-208, 302-304, 402-408 comprises at least three markers 210-216, 310-316, 410-416, each of the at least three markers 210-216, 310-316, 410-416 comprising location information with respect to the ultrasound probe 104. The method 500 may further comprise determining 512 whether the second ultrasound image dataset intersecting the at least three markers 210-216, 310-316, 410-416 added to the first mode image 202-208, 302-304, 402-408 is obtainable. The method 500 may further comprise causing 514 the display system 134 to present probe position feedback 430 based on the location information of each of the at least three markers 210-216, 310-316, 410-416 to guide manipulation of the ultrasound probe 104 to an updated position to acquire the second ultrasound image dataset intersecting the at least three markers 210-216, 310-316, 410-416 added to the first mode image 202-208, 302-304, 402-408.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for transposing markers added to a first ultrasound imaging mode dataset to a second ultrasound imaging mode dataset.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method, comprising:
acquiring, by an ultrasound probe of an ultrasound system, a first ultrasound image dataset according to a first mode;
processing, by at least one processor of the ultrasound system, the first ultrasound image dataset according to the first mode to generate a first mode image;
causing, by the at least one processor, a display system to present the first mode image;
adding, by the at least one processor, at least one marker to the first mode image in response to a user input;
receiving, by the at least one processor, a selection to switch to a second mode after the adding the at least one marker to the first mode image; and
in response to receiving the selection to switch to the second mode:
acquiring, by the ultrasound probe, a second ultrasound image dataset according to the second mode;
processing, by the at least one processor, the second ultrasound image dataset according to the second mode to generate a second mode image;
transposing, by the at least one processor, the at least one marker from the first mode image to the second mode image; and
causing, by the at least one processor, the display system to present the second mode image having the at least one marker transposed from the first mode image.

2. The method of claim 1, wherein the first mode is a two-dimensional (2D) mode and the second mode is a three-dimensional (3D) mode.

3. The method of claim 1, wherein the first mode is a 3D mode and the second mode is a 2D mode.

4. The method of claim 1, wherein:
the first ultrasound image dataset and the second ultrasound image dataset are acquired by the ultrasound probe at a same ultrasound probe position,
the at least one marker comprises location information with respect to the ultrasound probe, and
the transposing the at least one marker from the first mode image to the second mode image is based on the location information.

5. The method of claim 4, wherein the acquiring the second ultrasound image dataset is based on the location information of the at least one marker added to the first mode image such that the second mode image one or both of includes or intersects the at least one marker added to the first mode image.

6. The method of claim 1, wherein the at least one marker added to the first mode image comprises at least three markers, each of the at least three markers comprising location information with respect to the ultrasound probe, and further comprising:
determining, by the at least one processor, whether the second ultrasound image dataset intersecting the at least three markers added to the first mode image is obtainable; and
causing, by the at least one processor, the display system to present probe position feedback based on the location information of each of the at least three markers to guide manipulation of the ultrasound probe to an updated position to acquire the second ultrasound image dataset intersecting the at least three markers added to the first mode image.

7. An ultrasound system, comprising:
an ultrasound probe operable to:
acquire a first ultrasound image dataset according to a first mode; and
acquire a second ultrasound image dataset according to a second mode;
a display system; and
at least one processor configured to:
process the first ultrasound image dataset according to the first mode to generate a first mode image;
cause the display system to present the first mode image;
add at least one marker to the first mode image in response to a user input;
receive a selection to switch to the second mode after the at least one marker is added to the first mode image; and
in response to the selection to switch to the second mode:
cause the ultrasound probe to acquire the second ultrasound image dataset according to the second mode;
process the second ultrasound image dataset according to the second mode to generate the second mode image;
transpose the at least one marker from the first mode image to the second mode image, and
cause the display system to present the second mode image having the at least one marker transposed from the first mode image.

8. The system of claim 7, wherein the first mode is a 2D mode and the second mode is a 3D mode.

9. The system of claim 7, wherein the first mode is a 3D mode and the second mode is a 2D mode.

10. The system of claim 7, wherein:
the first ultrasound image dataset and the second ultrasound image dataset are acquired by the ultrasound probe at a same ultrasound probe position,
the at least one marker comprises location information with respect to the ultrasound probe, and
the transposing the at least one marker from the first mode image to the second mode image is based on the location information.

11. The system of claim 10, wherein the second ultrasound image dataset is acquired by the ultrasound probe based on the location information of the at least one marker added to the first mode image such that the second mode image one or both of includes or intersects the at least one marker added to the first mode image.

12. The system of claim 7, wherein:
the at least one marker added to the first mode image comprises at least three markers, each of the at least three markers comprising location information with respect to the ultrasound probe,
the at least one processor is configured to determine whether the second ultrasound image dataset intersecting the at least three markers added to the first mode image is obtainable; and
the at least one processor is configured to cause the display system to present probe position feedback based on the location information of each of the at least three markers to guide manipulation of the ultrasound probe to an updated position to acquire the second ultrasound image dataset intersecting the at least three markers added to the first mode image.

13. A non-transitory computer readable medium having stored thereon, a computer program having at least one code section, the at least one code section being executable by a machine for causing the machine to perform steps comprising:
- receiving a first ultrasound image dataset acquired according to a first mode;
- processing the first ultrasound image dataset according to the first mode to generate a first mode image;
- causing a display system to present the first mode image;
- adding at least one marker to the first mode image in response to a user input;
- receiving a selection to switch to a second mode after the at least one marker is added to the first mode image; and
- in response to receiving the selection to switch to the second mode:
  - receiving a second ultrasound image dataset acquired after the selection to switch and according to the second mode;
  - processing the second ultrasound image dataset according to the second mode to generate a second mode image;
  - transposing the at least one marker from the first mode image to the second mode image; and
  - causing the display system to present the second mode image having the at least one marker transposed from the first mode image.

14. The non-transitory computer readable medium of claim 13, wherein the first mode is a 2D mode and the second mode is a 3D mode.

15. The non-transitory computer readable medium of claim 13, wherein the first mode is a 3D mode and the second mode is a 2D mode.

16. The non-transitory computer readable medium of claim 13, wherein:
- the first ultrasound image dataset and the second ultrasound image dataset are acquired by an ultrasound probe at a same ultrasound probe position, the second ultrasound image dataset acquired based on the location information of the at least one marker added to the first mode image such that the second mode image one or both of includes or intersects the at least one marker added to the first mode image,
- the at least one marker comprises location information with respect to the ultrasound probe, and
- the transposing the at least one marker from the first mode image to the second mode image is based on the location information.

17. The non-transitory computer readable medium of claim 13, wherein the at least one marker added to the first mode image comprises at least three markers, each of the at least three markers comprising location information with respect to the ultrasound probe, and further comprising:
- determining whether the second ultrasound image dataset intersecting the at least three markers added to the first mode image is obtainable; and
- causing the display system to present probe position feedback based on the location information of each of the at least three markers to guide manipulation of the ultrasound probe to an updated position to acquire the second ultrasound image dataset intersecting the at least three markers added to the first mode image.

* * * * *